(12) United States Patent
Quartarone et al.

(10) Patent No.: US 10,670,442 B2
(45) Date of Patent: Jun. 2, 2020

(54) FUEL GAUGING SYSTEM AND IMPROVED METHODOLOGY FOR FUEL QUANTITY ESTIMATION

(71) Applicant: Simmonds Precision Products, Inc., Vergennes, VT (US)

(72) Inventors: Giusi Quartarone, Cork (IE); Radoslaw Zakrzewski, South Burlington, VT (US); Raymond Francis Foley, Cork (IE)

(73) Assignee: SIMMONDS PRECISION PRODUCTS, INC., Vergennes, VT (US)

( * ) Notice: Subject to any disclaimer, the term of this patent is extended or adjusted under 35 U.S.C. 154(b) by 136 days.

(21) Appl. No.: 15/635,558

(22) Filed: Jun. 28, 2017

(65) Prior Publication Data
US 2019/0003870 A1 Jan. 3, 2019

(51) Int. Cl.
| | | |
|---|---|---|
| G01F 23/00 | (2006.01) | |
| G01F 22/00 | (2006.01) | |
| G06N 3/04 | (2006.01) | |
| B64D 37/28 | (2006.01) | |
| B64D 37/00 | (2006.01) | |
| B64D 37/02 | (2006.01) | |
| G01N 33/22 | (2006.01) | |

(52) U.S. Cl.
CPC ....... *G01F 23/0061* (2013.01); *B64D 37/005* (2013.01); *B64D 37/02* (2013.01); *B64D 37/28* (2013.01); *G01F 22/00* (2013.01); *G01N 33/22* (2013.01); *G06N 3/0454* (2013.01)

(58) Field of Classification Search
CPC ...... B64D 37/02; G01F 23/0061; G01N 33/22
See application file for complete search history.

(56) References Cited

U.S. PATENT DOCUMENTS

| | | | | | |
|---|---|---|---|---|---|
| 5,138,559 | A | * | 8/1992 | Kuehl | G01F 23/0076 340/618 |
| 5,386,736 | A | * | 2/1995 | Spillman, Jr. | G01F 23/0076 73/149 |
| 6,157,894 | A | * | 12/2000 | Hess | B64D 37/00 702/141 |
| 6,502,042 | B1 | * | 12/2002 | Eid | G01F 23/0069 702/50 |

(Continued)

OTHER PUBLICATIONS

Extended European Search Report for European Application No. 18180372.7 dated Oct. 16, 2018; 43 Pages.

(Continued)

*Primary Examiner* — Manuel A Rivera Vargas
*Assistant Examiner* — Yaritza H Perez Bermudez
(74) *Attorney, Agent, or Firm* — Cantor Colburn LLP (57) ABSTRACT

An airplane is provided. The airplane includes a fuel gauging and quantity estimation system with an improved estimation accuracy. The fuel gauging and quantity estimation system operates by detecting an environment of a tank comprising a liquid and selecting one or more liquid gauging algorithms based on the environment. The fuel gauging and quantity estimation system further operates by receiving sensor data characterizing the liquid of the tank and utilizing the sensor data and the one or more liquid gauging algorithms to determine a property of the liquid.

18 Claims, 4 Drawing Sheets

(56) References Cited

U.S. PATENT DOCUMENTS

| | | | |
|---|---|---|---|
| 6,577,960 B1 * | 6/2003 | Rabelo | G01F 23/0069 |
| | | | 702/55 |
| 6,892,572 B2 | 5/2005 | Breed et al. | |
| 6,968,738 B2 * | 11/2005 | Atkinson | G01F 23/2962 |
| | | | 73/290 V |
| 7,680,617 B2 | 3/2010 | Mazrooee et al. | |
| 7,784,295 B2 | 8/2010 | McCormick et al. | |
| 8,798,976 B2 | 8/2014 | Ray et al. | |
| 2011/0087627 A1 | 4/2011 | Schmid et al. | |
| 2016/0238426 A1 * | 8/2016 | Tetil | G01F 23/0038 |

OTHER PUBLICATIONS

Jacobs et al.; "Task Decomposition Through Competition in a Modular Connectionist Architecture: The What and Where Vision Tasks"; Cognitive Science; vol. 15; 1991; pp. 219-250.

* cited by examiner

FIG. 1

FUEL GAUGING SYSTEM AND IMPROVED METHODOLOGY FOR FUEL QUANTITY ESTIMATION

BACKGROUND

A fuel mass within tanks of an aircraft determines in large measure a flight distance for the aircraft. Yet, measuring fuel mass, or any mass in a container, is a complicated process when a high accuracy is required. Complications arise from no sensor being able to directly measure a mass. Indeed, the mass is calculated based on a measurement of parameters that are related to the mass, such as by measuring the liquid height or volume and measuring a density value for the liquid.

In aircraft fuel gauging with contemporary aircraft applications, measuring fuel mass is further complicated by numerous other factors. The factors that complicate measuring fuel mass include complex tank geometry (which typically includes a number of interior structures), tank bending, aircraft dynamics maneuvers, fuel sloshing, acceleration effects, fuel density changes due to temperature, different fuel blends, and pressure variations with altitude and atmospheric conditions.

BRIEF DESCRIPTION

According to one or more embodiments, a processor-implemented method is provided. The processor-implemented method comprises detecting an environment of a tank comprising a liquid and selecting one or more liquid gauging algorithms based on the environment. The processor-implemented method comprises receiving sensor data characterizing the liquid of the tank and utilizing the sensor data and the one or more liquid gauging algorithms to determine a property of the liquid.

According to one or more embodiments or the above processor-implemented method, detecting the environment can comprise utilizing a relationship between an acceleration of the tank and pitch and roll angles of the tank to determine an effective attitude estimation.

According to one or more embodiments or any of the above processor-implemented method embodiments, the plurality of liquid gauging algorithms can comprise a plurality of neural networks, each neural network being designed to calculate the property based on a corresponding attitude range.

According to one or more embodiments or any of the above processor-implemented method embodiments, an attitude subset of each of the plurality of liquid gauging algorithms can overlap with an attitude subset of at least one other liquid gauging algorithm of the plurality of liquid gauging algorithms.

According to one or more embodiments or any of the above processor-implemented method embodiments, the attitude subset can comprise a single algorithm chosen based on attitude estimates relative to the attitude ranges of all algorithms.

According to one or more embodiments or any of the above processor-implemented method embodiments, the attitude subset can comprise one or more algorithms whose attitude ranges contain a current attitude estimate, and an output can be calculated by the one or more algorithms as a weighted sum based on where the current attitude estimate falls within an overlap.

According to one or more embodiments or any of the above processor-implemented method embodiments, the processor can execute a smoothed switching algorithm when the environment of the tank is between ranges.

According to one or more embodiments or any of the above processor-implemented method embodiments, the sensor data can comprise one or more of a pressure measurement, an acceleration measurement, and a fuel temperature measurement.

According to one or more embodiments or any of the above processor-implemented method embodiments, an aircraft can comprise the tank and the processor.

According to one or more embodiments, a fuel gauging and quantity estimation system is provided. The fuel gauging and quantity estimation system comprises a processor and a memory with program instructions thereon. The program instructions are executable by the processor to cause the fuel gauging and quantity estimation system to: detect an environment of a tank comprising a liquid; select one or more liquid gauging algorithms from a plurality of liquid gauging algorithms based on the environment; receive sensor data characterizing the liquid of the tank; and utilize the sensor data and the one or more liquid gauging algorithms to determine a property of the liquid.

According to one or more embodiments or the above fuel gauging and quantity estimation system embodiment, the detection of the environment can comprise utilizing a relationship between an acceleration of the tank and pitch and roll angles of the tank to determine an effective attitude estimation.

According to one or more embodiments or any of the above fuel gauging and quantity estimation system embodiments, the plurality of liquid gauging algorithms can comprise a plurality of neural networks, each neural network being designed to calculate the property based on a corresponding attitude range.

According to one or more embodiments or any of the above fuel gauging and quantity estimation system embodiments, an attitude subset of each of the plurality of liquid gauging algorithms can overlap with an attitude subset of at least one other liquid gauging algorithm of the plurality of liquid gauging algorithms.

According to one or more embodiments or any of the above fuel gauging and quantity estimation system embodiments, the attitude subset can comprise a single algorithm chosen based on attitude estimates relative to the attitude ranges of all algorithms.

According to one or more embodiments or any of the above fuel gauging and quantity estimation system embodiments, the attitude subset can comprise one or more algorithms whose attitude ranges contain a current attitude estimate, and an output can be calculated by the one or more algorithms as a weighted sum based on where the current attitude estimate falls within an overlap.

According to one or more embodiments or any of the above fuel gauging and quantity estimation system embodiments, the processor can execute a smoothed switching algorithm when the environment of the tank is between ranges.

According to one or more embodiments or any of the above fuel gauging and quantity estimation system embodiments, the sensor data can comprise one or more of a pressure measurement, an acceleration measurement, and a fuel temperature measurement.

According to one or more embodiments or any of the above fuel gauging and quantity estimation system embodiments, an aircraft can comprise the tank and the fuel gauging and quantity estimation system.

According to one or more embodiments, a computer program product is provided. The computer program product comprises a computer readable storage medium having program instructions embodied therewith. The program instructions are executable by a processor to cause the processor to: detect an environment of a tank comprising a liquid; select one or more liquid gauging algorithms from a plurality of liquid gauging algorithms based on the environment; receive sensor data characterizing the liquid of the tank; and utilize the sensor data and the one or more liquid gauging algorithms to determine a property of the liquid.

According to one or more embodiments or the above computer program product embodiment, the detection of the environment can comprise utilizing a relationship between an acceleration of the tank and pitch and roll angles of the tank to determine an effective attitude estimation.

BRIEF DESCRIPTION OF THE DRAWINGS

The subject matter is particularly pointed out and distinctly claimed in the claims at the conclusion of the specification. The forgoing and other features, and advantages thereof are apparent from the following detailed description taken in conjunction with the accompanying drawings in which:

DETAILED DESCRIPTION

A detailed description of one or more embodiments of the disclosed apparatus and method are presented herein by way of exemplification and not limitation with reference to the FIGS.

Embodiments herein provide a fuel gauging and quantity estimation system of an aircraft with improved estimation accuracy. According to one or more embodiments, the fuel gauging and quantity estimation system can be utilized in an aerospace application (e.g., pressure-based fuel gauging system); however, the fuel gauging and quantity estimation system is not limited to, as it can be used for other applications where the liquid quantity, within a container or tank, is estimated.

Figure 1:
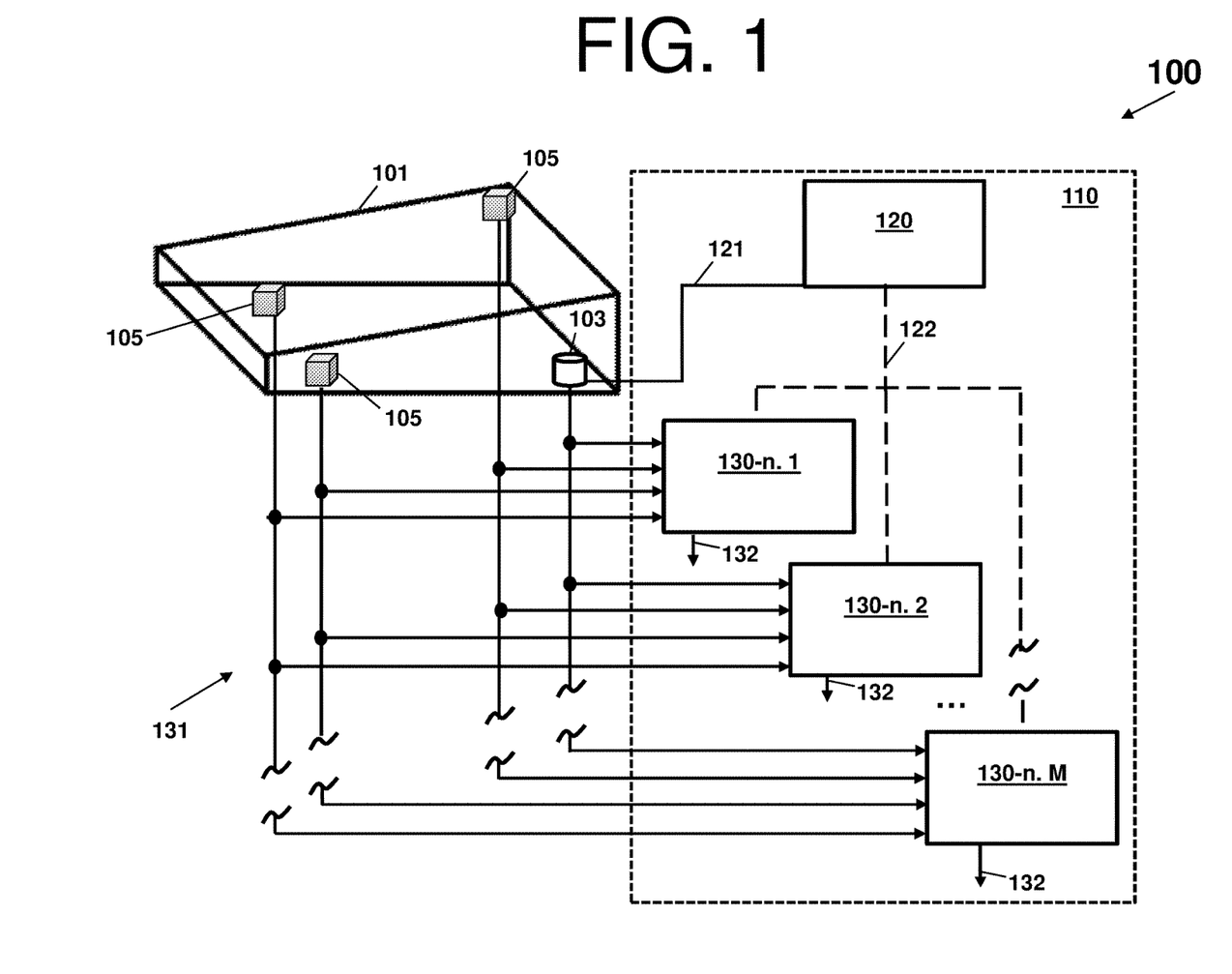
FIG. 1 depicts a diagram of a fuel gauging and quantity estimation system according to one or more embodiments.

Turning now to FIG. 1, a diagram of a fuel gauging and quantity estimation system 100 according to one or more embodiments. As noted herein, the fuel gauging and quantity estimation system 100 can be installed on an aircraft, but is not limited thereto.

The fuel gauging and quantity estimation system 100 comprises a tank 101 with at least one sensor 103 and one or more parameter sensors 105 associated therewith. The tank 101 can be a container, of any shape or size, capable of holding a fluid (e.g., liquid or gas). The tank 101, in the embodiments herein but not limited thereto, can be a fuel tank that is part of an engine system of the aircraft.

The at least one sensor 103 and the one or more parameter sensors 105 can be referred to, generally, as sensors. A sensor can be an electro-mechanical component that detects events or changes in an environment and outputs the events or changes as sensor signals to other components of the fuel gauging and quantity estimation system 100. In accordance with one or more embodiments, the at least one sensor 103 and the one or more parameter sensors 105 can detect events or changes regarding the tank 101, an environment of the tank 101, and a liquid property with respect to motion, temperature, liquid density, liquid type, tank liquid content, altitude, acceleration, pressure, tank bending, vibration, light, magnetic fields, gravity, humidity, moisture, electrical fields, sound, stretch, position, etc. In accordance with one or more embodiments (and as shown in FIG. 1), the tank 101 is associated with four sensors: three pressure sensors (represented by cubes; the parameter sensors 105) and one accelerometer (represented by a cylinder; the sensor 103). The at least one sensor 103 and the one or more parameter sensors 105 communicate with a selection sub-system 110.

The selection sub-system 110 comprises a selection controller 120 that receives outputs 121 from the at least one sensor 103. The selection controller 120 can be electronic circuitry and/or software, as described herein. The selection sub-system 110 also comprises a plurality of liquid gauging algorithms 130 (e.g., a liquid gauging algorithm 130-n.1, a liquid gauging algorithm 130-n.2, a liquid gauging algorithm 130-n.M, where is M is an integer) that are selected via the selection signal 122 by the selection controller 120 in accordance with the output 121 of the at least one sensor 103. For example, measurements from the one accelerometer (represented by a cylinder; the sensor 103) are used for selecting one of the plurality of liquid gauging algorithms 130 (e.g., the selected liquid gauging algorithm). The plurality of liquid gauging algorithms 130 can provide an output 132.

Once selected, a liquid gauging algorithm (or liquid gauging algorithms) of plurality of liquid gauging algorithms 130 receives sensor data 131 characterizing liquid/fuel contained in the tank 101. Note that the sensor data 131 directly varies according to a quantity and properties of the liquid/fuel contained in the tank 101. In this way, the environment/parameters of the tank 101 are used to select the liquid gauging algorithm, which combines those parameters with the sensor data 131 characterizing the liquid/fuel contained in the tank 101.

The liquid gauging algorithm utilizes the sensor data 131 to determine a property of the liquid within the tank 101 (such as mass, volume, and density of the liquid within the tank 101). That is, with respect to the fuel tank example herein, a fuel mass is estimated by using the selected liquid gauging algorithm and the measurements from the pressure sensors (represented by cubes; the parameter sensors 105) within the tank 101.

Figure 2:
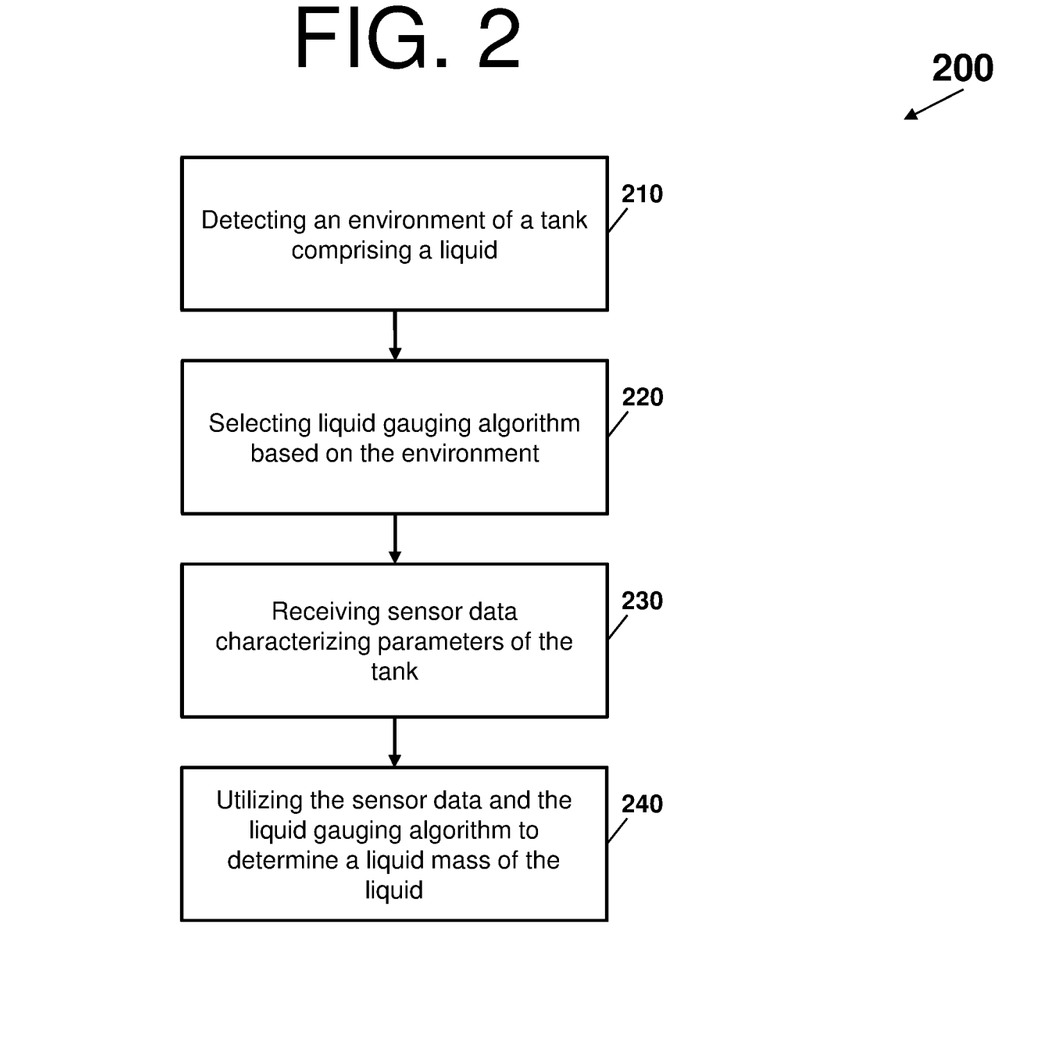
FIG. 2 depicts a process flow for determining a property of a liquid within a tank according to one or more embodiments.

Turning now to FIG. 2, a process flow 200 for determining a property of the liquid within the tank 101 is depicted according to one or more embodiments. The process flow 200 begins at block 210, where the fuel gauging and quantity estimation system 100 detects an environment of the tank 101 comprising a liquid. The environment of the tank 101 can correspond to an effective attitude estimation of the tank 101. Note that the process flow 200 resolves a number of challenges with respect to estimating the effective attitude estimation, as the effective tank attitude can be estimated in different ways or provided/measured by other systems (e.g., provided by an aircraft navigation system).

In accordance with one or more embodiments, the detection of the environment can comprise utilizing a relationship between an acceleration of the tank 101 and pitch and roll angles of the tank 101 to determine the effective attitude estimation. For instance, the effective attitude estimation can be determined by trigonometric relationships between the acceleration of the tank 101 and the pitch and roll angles of the tank 101. The trigonometric relationships can map an aircraft acceleration $a_x$, $a_y$, and $a_z$ with an effective pitch $\tilde{P}$ and an effective roll $\tilde{R}$, which can depend on modelling tank rotations.

Note that because the measurements by the accelerometer can be affected by an error, a real effective attitude (P and R) differs from the effective attitude estimation ($\tilde{P}$ and $\tilde{R}$). In particular, the effective attitude estimation is affected by an error with respect to a number of accelerometers installed and their accuracy. In turn, the fuel gauging and quantity estimation system 100 can assume that all values for the real effective pitch are between $P \in \tilde{P} \pm \Delta$ and that all the values for the effective roll are between $R \in \tilde{R} \pm \Delta$, where $\Delta$ represents a maximum attitude estimation error that is possible based on the available accelerometers. Generally, a higher number of accelerometers with a higher accuracy results in a smaller $\Delta$.

At block 220, the fuel gauging and quantity estimation system 100 selects a liquid gauging algorithm (or liquid gauging algorithms) from the plurality of liquid gauging algorithms 130 based on the environment. Each liquid gauging algorithm can be designed to calculate a property of the liquid based on a corresponding pitch range. That is, the environment of the tank 101 can be referred to as an attitude of the tank 101. The range of attitudes thus corresponds to a range of environments. Other examples of range of environments can include, but are not limited to, range of altitude, range of tank liquid content, range of liquid temperature, range of liquid type, etc. The range of attitudes is divided into subsets. Each subset can be preassigned a liquid gauging algorithm, such that the plurality of liquid gauging algorithms 130 matches an entire range of attitudes. In this way, as the effective attitude estimation of block 210 falls within one or more of the pitch ranges (i.e., subsets of attitudes) the corresponding liquid gauging algorithm is selected.

A number of subsets or an amplitude of each subset, depends on a desired accuracy level, on a complexity of a problem that is addressed, and/or on an intrinsic accuracy of the gauging algorithms. With respect to determining an amplitude of each attitude subset, a higher number of subsets results in a higher estimation accuracy until a maximum accuracy level is reached. Also, a higher number of accurate accelerometers results in a smaller overlapping range. Above a maximum accuracy level, accuracy depends on a number of sensors and an accuracy of those (rather than the number of gauging algorithms used).

The plurality of liquid gauging algorithms 130 can comprise a plurality of neural networks (but not limited thereto; note that the plurality of liquid gauging algorithms 130 can also comprise one or more of neural networks, nonlinear models, linear models, etc.). For instance, each neural network is trained to estimate a property of the liquid of the tank 101 for a subset of attitudes. Note, for each subset, a neural network is trained and stored in a memory of a processor installed within the fuel gauging and quantity estimation system 100. In turn, a number of neural networks can be determined with respect to desired estimation accuracy and an occupied memory. Further, the fuel gauging and quantity estimation system 100 increases the estimation accuracy by using multiple neural networks, rather just a single neural network. When more neural networks are used, each neural network is less complex because it is representative of a smaller portion of an entire system. Indeed, each neural network is responsible to estimate the property for a subset of attitudes.

An attitude subset of each of the plurality of liquid gauging algorithms 130 can overlap with an attitude subset of at least one other liquid gauging algorithm of the plurality of liquid gauging algorithms 130. Note that the overlapping ranges can include other ranges of environment, such as fuel density, altitude, tank fuel volume, etc. in accordance with one or more embodiments. Also, note that the overlap between ranges depends on the type of range of environment.

Figure 3:
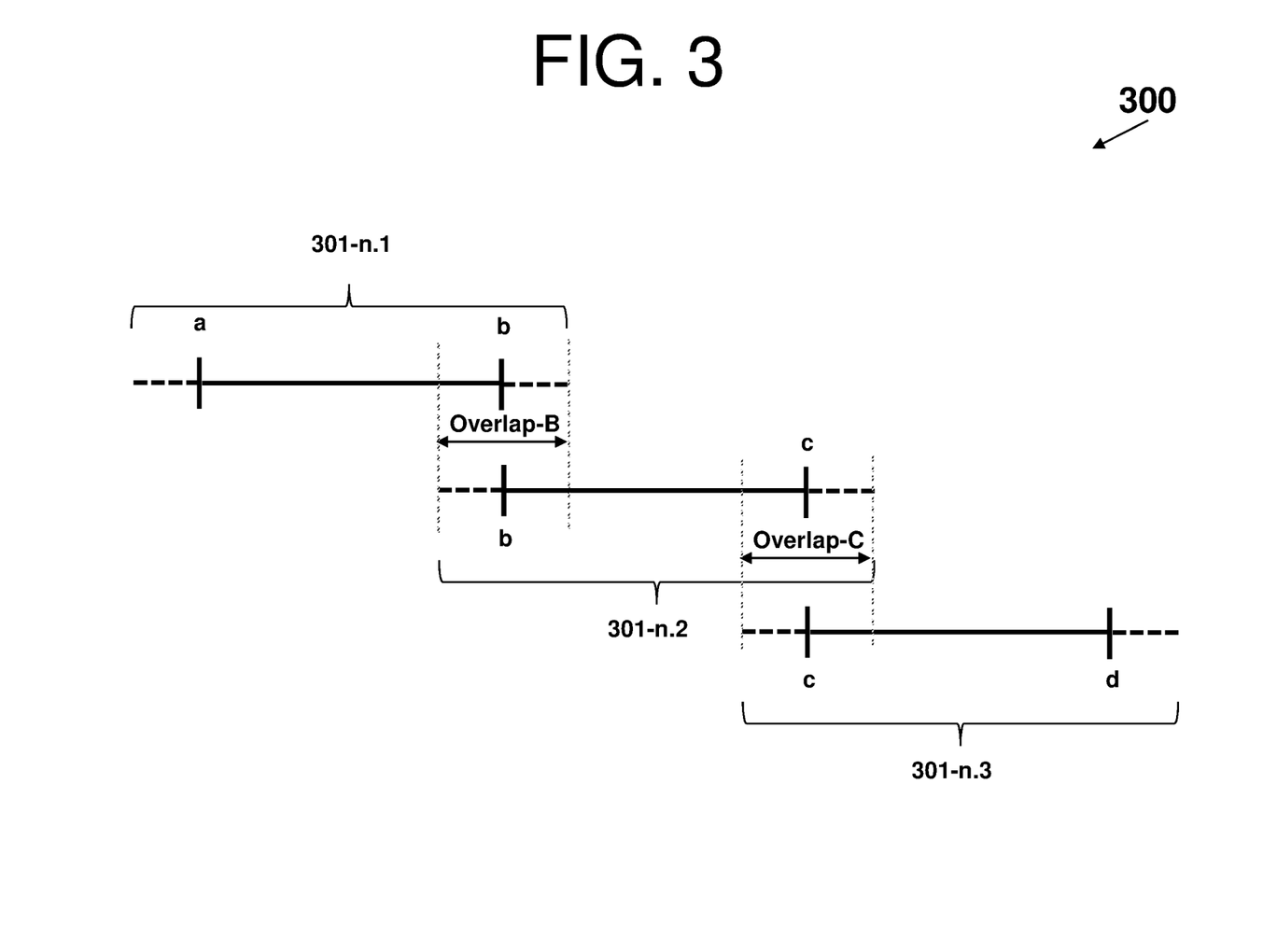
FIG. 3 depicts a pitch overlapping diagram of a fuel gauging and quantity estimation system according to one or more embodiments.

FIG. 3 depicts a pitch overlapping example 300 of the fuel gauging and quantity estimation system 100 according to one or more embodiments. The pitch overlapping example 300 comprises three pitch ranges: a first pitch range 301-n.1, a second pitch range 301-n.2, and a third pitch range 301-n.3. The overlapping amplitude (e.g., Overlap-B and Overlap-C) between the first pitch range 301-n.1, the second pitch range 301-n.2, and the third pitch range 301-n.3 is greater than or equal to $2\Delta$, where $\Delta$ is the maximum effective attitude estimation error that is possible based on the current accelerometers suite. Similarly, a roll sub-ranges overlapping can be utilized.

When the real effective attitude is close to the boundary of two different subsets, there is no guarantee that the estimated effective attitude will bring to the selection of the correct neural network. Therefore, to avoid the selection of the wrong neural network, the subsets of effective attitudes overlap each other by a quantity greater or equal than $2\Delta$. Note that each subset generally overlaps along the two ends with two other neural networks (unless the range represents an extreme attitude condition).

In view of the above, selecting the liquid gauging algorithm from the plurality of liquid gauging algorithms 130 can comprise: knowledge of the effective pitch $\tilde{P}$ and roll $\tilde{R}$ (by estimation or from another system), calculation of the pitch and roll range of uncertainty: $P \in \tilde{P} \pm \Delta$ and $R \in \tilde{R} \pm \Delta$, and/or selection of the liquid gauging algorithm that has been entirely trained for both ranges of uncertainty. Note that if more than one accelerometer is used by the gauging algorithm, proper precaution has to be taken to avoid liquid gauging algorithm selection problems when one or more accelerometers fail. In this scenario, $\Delta$ should represent the maximum attitude estimation error when the only accelerometer with worst accuracy is properly working.

Note that the selecting of the liquid gauging algorithm from the plurality of liquid gauging algorithms 130 can address the issue of uncertainty, where the fuel gauging and quantity estimation system 100 uses the correct neural network (or gauging algorithm) trained on an entire uncertainty range. However, relying on a single neural network can result in an undesirable "switching" scenario, where a small change in attitude measurement may cause the algorithm to be switched from one neural network to another (due to the environment of the tank being between ranges or on the overlapping portion of the ranges). This switching may occur one or more times and lead to unwanted "oscillations" in neural network outputs. Thus, a "smoothed" switching can be utilized by the fuel gauging and quantity estimation system 100.

In accordance with one or more embodiments, the fuel gauging and quantity estimation system 100 can calculate the liquid quantity as a weighted sum of outputs of two gauging algorithms whose environmental ranges overlap (e.g., as an alternative to selecting a single liquid gauging algorithm from plurality of liquid gauging algorithms 130, within overlap regions). The weighting factors can be determined based on the relative position of the effective attitude estimates relative to the boundaries of overlap region. For example, referring back to FIG. 3, if the effective pitch estimate lies exactly in the middle of the Overlap B region, at point b, then the weight applied to the output of algorithm 301-n.1 may be 0.5 and the weight applied to the output of algorithm 301-n.2 may be also 0.5, so that the output of the fuel gauging and quantity estimation system 100 is an average of the two outputs. Then, as the effective pitch estimate moves away from the point b leftwards, the weight applied to the output of algorithm 301-n.1 may be increasing from 0.5 towards 1 and the weight applied to the output of algorithm 301-n.2 may be decreasing from 0.5 to 0, so that their sum remains equal to 1. At the left-hand end of the Overlap B region, the weight applied to the output of algorithm 301-n.1 may be 1.0 and the weight applied to the output of algorithm 301-n.2 may be also 0. The changes of both weighting factors can be calculated proportionally according to the distance between the current effective pitch estimate and the mid-point b. In this way, the fuel gauging and quantity estimation system 100 can allow for smoothed or soft transition between two gauging algorithms and can minimize the undesired jumps in the estimated liquid quantity at the boundary regions. For instance, a smoothed switching algorithm of the fuel gauging and quantity estimation system 100 can select a subset of algorithms trained on overlapping regions and calculate a weighted sum of the outputs of the subset of algorithms based on the effective attitude estimates relative to the boundaries of the overlap region.

Note that any other suitable distance-based weighted sum algorithm can be utilized by the fuel gauging and quantity estimation system 100. Also note that even though FIG. 3 refers to pitch angle estimation, the same weighted sum approach can be used for roll estimation and/or other estimations. For instance, the two-dimensional overlap may require considering four distinct gauging algorithms trained for four overlapping environmental ranges. Further, any two-dimensional smoothing approach may be used, such as bilinear interpolation.

At block 230, the fuel gauging and quantity estimation system 100 receives the sensor data 131 characterizing parameters (set of system conditions) of the tank 101. The sensor data 131 can comprise one or more of a pressure measurement, an acceleration measurement (along the three directions), and a fuel temperature measurements (when available).

At block 240, the fuel gauging and quantity estimation system 100 utilizes the sensor data 131 and the liquid gauging algorithm to determine a property (or other quantity of interest) of the liquid. The selected liquid gauging algorithms (from multiple algorithms) from block 220 receive as input the pressure measurements, the acceleration measurements, and/or the fuel temperature measurements.

Technical effects and benefits of a fuel gauging and quantity estimation system embodiments include a reduction in a number of sensors within the tank and/or to use less accurate sensors (generally less expensive) due to the improved accuracy. Note that reducing the number of sensors results in a reduction of the sensors installation time and, moreover, improves a reliability of the fuel gauging and quantity estimation system, since fewer components are installed within the tank. Additionally, the fuel gauging and quantity estimation system can support sensors with a lower accuracy, whilst guaranteeing a proper estimation accuracy. Note that, according to one or more embodiments, the fuel gauging and quantity estimation system can be applied to any other system where a liquid quantity is measured by using different sensor technologies and different gauging algorithms. Further, embodiments described herein are necessarily rooted in selection sub-system of the fuel gauging and quantity estimation system to perform proactive operations to overcome problems specifically arising in the realm of fuel gauging and quantity estimation.

Figure 4:
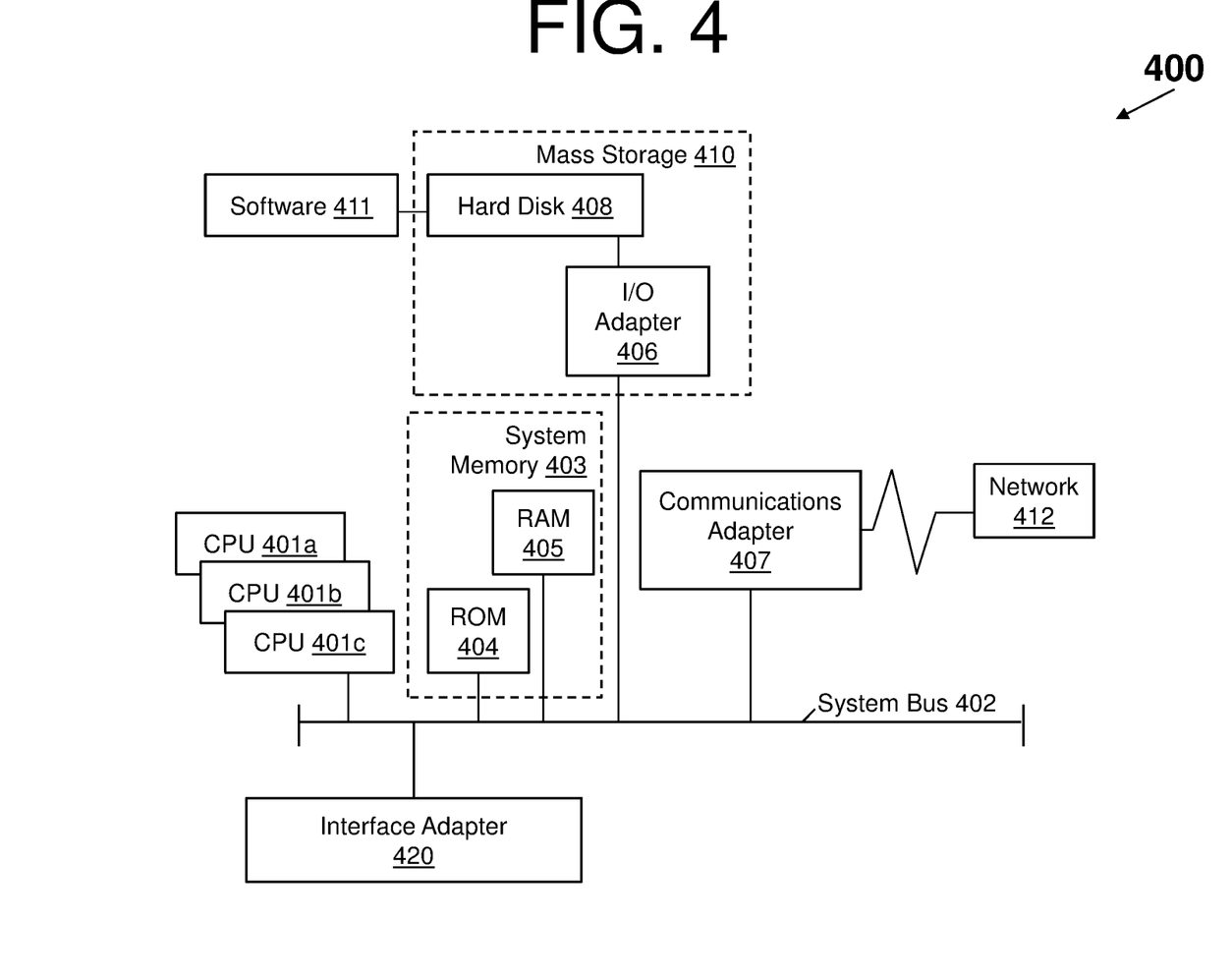
FIG. 4 depicts an architecture of a fuel gauging and quantity estimation system according to one or more embodiments.

FIG. 4 depicts a system 400 that supports the selection sub-system 110 in accordance with one or more embodiments. The system 400 has one or more central processing units (CPU(s)) 401a, 401b, 401c, etc. (collectively or generically referred to as processor(s) 401). The processors 401, also referred to as processing circuits, are coupled via a system bus 402 to system memory 403 and various other components. The system memory 403 can include a read only memory (ROM) 404 and a random access memory (RAM) 405. The ROM 404 is coupled to the system bus 402 and may include a basic input/output system (BIOS), which controls certain basic functions of the system 400. The RAM is read-write memory coupled to the system bus 402 for use by the processors 401.

FIG. 4 further depicts an input/output (I/O) adapter 406 and a communications adapter 407 coupled to the system bus 402. The I/O adapter 406 may be a small computer system interface (SCSI) adapter that communicates with a hard disk 408 and/or any other similar component. The I/O adapter 406 and the hard disk 408 are collectively referred to herein as a mass storage 410. Software 411 for execution on the system 400 may be stored in the mass storage 410. The mass storage 410 may also store the one or more liquid gauging algorithms. The mass storage 410 is an example of a tangible storage medium readable by the processors 401, where the software 411 is stored as instructions for execution by the processors 401 to cause the system 400 to operate, such as is described herein with reference to FIG. 3. Examples of computer program product and the execution of such instruction is discussed herein in more detail. Referring again to FIG. 4, a communications adapter 407 interconnects the system bus 402 with a network 412, which may be an outside network, enabling the system 400 to communicate with other such systems. In one embodiment, the adapters 406 and 407 may be connected to one or more I/O buses that are connected to the system bus 402 via an intermediate bus bridge (not shown). Suitable I/O buses for connecting peripheral devices such as hard disk controllers and network adapters typically include common protocols, such as the Peripheral Component Interconnect (PCI). Additional input/output devices are shown as connected to the system bus 402 via an interface adapter 420, which may include, for example, a Super I/O chip integrating multiple device adapters into a single integrated circuit. Sensors associated with an aircraft and/or a tank of the aircraft can also be interconnected to the system bus 402 via the interface adapter 420.

Thus, as configured in FIG. 4, the system 400 includes processing capability in the form of the processors 401, and storage capability including the system memory 403 and the mass storage 410. In one embodiment, a portion of the system memory 403 and the mass storage 410 collectively store an operating system to coordinate the functions of the various components shown in FIG. 4.

Embodiments herein may be a system, a method, and/or a computer program product at any possible technical detail level of integration. The computer program product may include a computer readable storage medium (or media)

having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the embodiments are described herein with reference to flowchart illustrations, schematics, and/or block diagrams of methods, apparatus, and/or systems according to embodiments. Further, the descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The flow diagrams depicted herein are just one example. There may be many variations to this diagram or the steps (or operations) described therein without departing from the spirit of embodiments herein. For instance, the steps may be performed in a differing order or steps may be added, deleted or modified. All of these variations are considered a part of the claims.

While the preferred embodiment has been described, it will be understood that those skilled in the art, both now and in the future, may make various improvements and enhancements which fall within the scope of the claims which follow. These claims should be construed to maintain the proper protection.

What is claimed is:

1. A processor-implemented method comprising:
   determining, by a processor, an environment of a tank comprising a liquid,
   wherein the environment of the tank comprises a current effective attitude of the tank;
   determining a plurality of liquid gauging algorithms comprising a first liquid gauging algorithm, wherein the first liquid gauging algorithm in the plurality of liquid gauging algorithms is associated with a first attitude range in a set of attitude ranges;
   selecting, by the processor, the first liquid gauging algorithms from the plurality of liquid gauging algorithms based on the current effective attitude of the tank being within the first attitude range;
   receiving, by the processor, sensor data characterizing the liquid of the tank;
   utilizing, by the processor, the sensor data and the first liquid gauging algorithms to determine a property of the liquid;
   wherein at least one attitude range is the set of attitude ranges overlaps with another attitude range in the set of attitude ranges defining an range overlap region; and
   wherein the processor executes a smoothed switching algorithm when the current effective attitude of the tank is within the range overlap region, wherein the smooth switching algorithm comprises two liquid gauging algorithms.

2. The processor-implemented method of claim 1, wherein detecting the environment comprises utilizing a relationship between an acceleration of the tank and pitch and roll angles of the tank to determine the current effective attitude of the tank.

3. The processor-implemented method of claim 1, wherein the plurality of liquid gauging algorithms comprises a plurality of neural networks, each neural network being designed to calculate the property based on a corresponding attitude range in the set of attitude ranges.

4. The processor-implemented method of claim 1, wherein an attitude subset of each of the plurality of liquid gauging algorithms overlaps with an attitude subset of at least one other liquid gauging algorithm of the plurality of liquid gauging algorithms.

5. The processor-implemented method of claim 4, wherein the attitude subset comprises a single algorithm chosen based on attitude estimates relative to the attitude ranges of all algorithms.

6. The processor-implemented method of claim 4, wherein an output is calculated by the first liquid gauging algorithms as a weighted sum based on where the current effective attitude falls within an overlap.

7. The processor-implemented method of claim 1, wherein the sensor data comprises one or more of a pressure measurement, an acceleration measurement, and a fuel temperature measurement.

8. The processor-implemented method of claim 1, wherein an aircraft comprises the tank and the processor.

9. A fuel gauging and quantity estimation system comprising a processor and a memory with program instructions thereon, the program instructions executable by the processor to cause the fuel gauging and quantity estimation system to:
   determine an environment of a tank comprising a liquid, wherein the environment of the tank comprises a current effective attitude of the tank;
   determine a plurality of liquid gauging algorithms comprising a first liquid gauging algorithm, wherein the first liquid gauging algorithm in the plurality of liquid gauging algorithms is associated with a first attitude range in a set of attitude ranges;
   select the first liquid gauging algorithms from the plurality of liquid gauging algorithms based on the current effective attitude of the tank being within the first attitude range;
   receive sensor data characterizing the liquid of the tank; and
   utilize the sensor data and the first liquid gauging algorithms to determine a property of the liquid;
   wherein at least one attitude range is the set of attitude ranges overlaps with another attitude range in the set of attitude ranges defining an range overlap region; and
   wherein the processor executes a smoothed switching algorithm when the current effective attitude of the tank is within the range overlap region, wherein the smooth switching algorithm comprises two liquid gauging algorithms.

10. The fuel gauging and quantity estimation system of claim 9, wherein detection of the environment comprises utilizing a relationship between an acceleration of the tank and pitch and roll angles of the tank to determine the current effective attitude of the tank.

11. The fuel gauging and quantity estimation system of claim 9, wherein the plurality of liquid gauging algorithms comprises a plurality of neural networks, each neural network being designed to calculate the property based on a corresponding attitude range in the set of attitude ranges.

12. The fuel gauging and quantity estimation system of claim 9, wherein an attitude subset of each of the plurality of liquid gauging algorithms overlaps with an attitude subset of at least one other liquid gauging algorithm of the plurality of liquid gauging algorithms.

13. The fuel gauging and quantity estimation system of claim 12, wherein the attitude subset comprises a single algorithm chosen based on attitude estimates relative to the attitude ranges of all algorithms.

14. The fuel gauging and quantity estimation system of claim 12,
   wherein an output is calculated by the first liquid gauging algorithms as a weighted sum based on where the current effective attitude falls within an overlap.

15. The fuel gauging and quantity estimation system of claim 9, wherein the sensor data comprises one or more of a pressure measurement, an acceleration measurement, and a fuel temperature measurement.

16. The fuel gauging and quantity estimation system of claim 9, wherein an aircraft comprises the tank and the fuel gauging and quantity estimation system.

17. A computer program product, the computer program product comprising a computer readable storage medium having program instructions embodied therewith, the program instructions executable by a processor to cause the processor to:
   determine an environment of a tank comprising a liquid, wherein the environment of the tank comprises a current effective attitude of the tank;
   determine a plurality of liquid gauging algorithms comprising a first liquid gauging algorithm, wherein the first liquid gauging algorithm in the plurality of liquid gauging algorithms is associated with a first attitude range in a set of attitude ranges;
   select the first liquid gauging algorithms from the plurality of liquid gauging algorithms based on the current effective attitude of the tank being within the first attitude range;
   receive sensor data characterizing the liquid of the tank; and
   utilize the sensor data and the first liquid gauging algorithms to determine a property of the liquid;
   wherein at least one attitude range is the set of attitude ranges overlaps with another attitude range in the set of attitude ranges defining an range overlap region; and
   wherein the processor executes a smoothed switching algorithm when the current effective attitude of the tank is within the range overlap region, wherein the smooth switching algorithm comprises two liquid gauging algorithms.

18. The computer program product of claim 17, wherein detection of the environment comprises utilizing a relationship between an acceleration of the tank and pitch and roll angles of the tank to determine the current effective attitude.

* * * * *